US008067397B2

(12) United States Patent  (10) Patent No.: US 8,067,397 B2
Attawia et al.  (45) Date of Patent: *Nov. 29, 2011

(54) TRANSDISCAL ADMINISTRATION OF CYCLINE COMPOUNDS

(75) Inventors: Mohamed Attawia, Holmdel, NJ (US); Thomas M. DiMauro, Southborough, MA (US); Hassan Serhan, South Easton, MA (US); Sudhakar Kadiyala, Newton, MA (US); David Urbahns, Barrington, RI (US); Gregory Collins, East Sandwich, MA (US); Laura J. Brown, Hamilton Square, NJ (US); Jeffrey C. Geesin, Doylestown, PA (US)

(73) Assignee: DePuy Spine, Inc., Raynham, MA (US)

( * ) Notice: Subject to any disclaimer, the term of this patent is extended or adjusted under 35 U.S.C. 154(b) by 42 days.

This patent is subject to a terminal disclaimer.

(21) Appl. No.: 12/454,200

(22) Filed: May 14, 2009

(65) Prior Publication Data

US 2009/0324558 A1    Dec. 31, 2009

Related U.S. Application Data

(62) Division of application No. 10/640,412, filed on Aug. 13, 2003, now Pat. No. 7,553,827.

(51) Int. Cl.
*A61K 31/65* (2006.01)
*A61K 38/46* (2006.01)
(52) U.S. Cl. ............... 514/152; 514/154; 424/94.65
(58) Field of Classification Search .......... 514/152, 514/154; 424/94.65
See application file for complete search history.

(56) References Cited

U.S. PATENT DOCUMENTS

| | | |
|---|---|---|
| 3,678,158 A | 7/1972 | Sussman |
| 4,341,867 A | 7/1982 | Johansen |
| 4,427,649 A | 1/1984 | Dingle et al. |
| 4,435,506 A | 3/1984 | Jackson et al. |
| 4,696,816 A | 9/1987 | Brown |
| 5,095,037 A | 3/1992 | Iwamitsu et al. |
| 5,116,964 A | 5/1992 | Capon et al. |
| 5,194,596 A | 3/1993 | Tischer et al. |
| 5,223,248 A | 6/1993 | McNamara et al. |
| 5,225,538 A | 7/1993 | Capon et al. |
| 5,231,024 A | 7/1993 | Moeller et al. |
| 5,258,371 A | 11/1993 | Golub et al. |
| 5,270,300 A | 12/1993 | Hunziker |
| 5,368,841 A | 11/1994 | Trauner et al. |
| 5,447,851 A | 9/1995 | Beutler et al. |
| 5,510,370 A | 4/1996 | Hock |
| 5,602,156 A | 2/1997 | Kohn et al. |
| 5,656,272 A | 8/1997 | Le et al. |
| 5,656,644 A | 8/1997 | Adams et al. |
| 5,728,396 A | 3/1998 | Peery et al. |
| 5,833,984 A | 11/1998 | Eibl et al. |
| 5,842,477 A | 12/1998 | Naughton et al. |
| 5,942,499 A | 8/1999 | Radomsky |
| 5,965,583 A | 10/1999 | Beers et al. |
| 6,049,026 A | 4/2000 | Muschler |
| 6,277,969 B1 | 8/2001 | Le et al. |
| 6,284,471 B1 | 9/2001 | Le et al. |
| 6,294,170 B1 | 9/2001 | Boone et al. |
| 6,300,347 B1 | 10/2001 | Revesz |
| 6,340,369 B1 | 1/2002 | Ferree |
| 6,352,557 B1 | 3/2002 | Ferree |
| 6,419,944 B2 | 7/2002 | Tobinick |
| 6,541,477 B2 | 4/2003 | Lewicki et al. |
| 6,554,830 B1 | 4/2003 | Chappius |
| 6,590,081 B1 | 7/2003 | Zhang |
| 6,593,310 B1 | 7/2003 | Cullis-Hill |
| 6,623,472 B1 | 9/2003 | Reincke et al. |
| 6,713,246 B1 | 3/2004 | Reinecke et al. |
| 6,756,215 B1 | 6/2004 | Wolfraim et al. |
| 7,067,144 B2 | 6/2006 | Demopulos et al. |
| 7,344,716 B2 | 3/2008 | DiMauro et al. |
| 7,429,378 B2 * | 9/2008 | Serhan et al. .............. 424/94.65 |
| 7,553,827 B2 | 6/2009 | Attawia et al. |
| 7,799,782 B2 | 9/2010 | Munson et al. |
| 2001/0006948 A1 | 7/2001 | Kang et al. |
| 2001/0016195 A1 | 8/2001 | Tobinick |
| 2001/0026801 A1 | 10/2001 | Tobinick |
| 2002/0010471 A1 | 1/2002 | Wironen et al. |
| 2002/0019351 A1 | 2/2002 | Ke et al. |
| 2002/0026244 A1 | 2/2002 | Trieu |
| 2002/0032155 A1 | 3/2002 | Ferree |
| 2002/0082697 A1 | 6/2002 | Damien |
| 2002/0107200 A1 | 8/2002 | Chang et al. |
| 2002/0169162 A1 | 11/2002 | Smith et al. |
| 2002/0198599 A1 | 12/2002 | Haldimann |

(Continued)

FOREIGN PATENT DOCUMENTS

AU    2003/263340 A1    3/2004

(Continued)

OTHER PUBLICATIONS

Abbas-Ghaleb, K., et al., "Preconcentration of Selenium Compounds on a Porous Graphitic Carbon Column in View of HPLC-ICP-AES Speciation Analysis," *Anal. Bioanal. Chem.*, 377: 1026-1031 (2003).

Ahn, N., et al., "Effect of Nutrient Concentration and OP-1 on the Metabolism of Intervertebral Disc: In Vitro Organ Culture Study," 28, *Abstracts of the 30th Annual Meeting of the International Society for the Study of the Lumbar Spine*, Vancouver, Canada (May 2003).

Alini, M., et al., "A Biological Approach in Treating Disc Degeneration: Not for Today, but Maybe for Tomorrow," *Eur. Spine J.*, 11(Supp. 2): S215-S220 (2002).

Allali, F., et al., "Increase in Bone Mineral Density of Patients with Spondyloarthropathy Treated with Anti-tumour Necrosis Factor α, "*Ann. Rheum. Dis.*, 62: 347-349 (2003).

(Continued)

*Primary Examiner* — Raymond Henley, III
(74) *Attorney, Agent, or Firm* — Hamilton, Brook, Smith & Reynolds, P.C.

(57) ABSTRACT

The present invention relates to administering a doxycycline compound into a diseased intervertebral disc.

20 Claims, No Drawings

U.S. PATENT DOCUMENTS

| | | |
|---|---|---|
| 2003/0007972 A1 | 1/2003 | Tobinick |
| 2003/0039651 A1 | 2/2003 | Olmarker |
| 2003/0049256 A1 | 3/2003 | Tobinick |
| 2003/0069639 A1 | 4/2003 | Sander et al. |
| 2003/0134792 A1 | 7/2003 | Pike et al. |
| 2003/0207827 A1 | 11/2003 | Boyle et al. |
| 2003/0220692 A1 | 11/2003 | Shapiro et al. |
| 2004/0022864 A1 | 2/2004 | Freyman et al. |
| 2004/0126372 A1 | 7/2004 | Banerjee et al. |
| 2004/0193274 A1 | 9/2004 | Trieu |
| 2004/0228853 A1 | 11/2004 | Serhan et al. |
| 2004/0229786 A1 | 11/2004 | Attawia et al. |
| 2004/0229878 A1 | 11/2004 | DiMauro et al. |
| 2005/0025765 A1 | 2/2005 | DiMauro et al. |
| 2005/0038001 A1 | 2/2005 | Attawia et al. |
| 2005/0054595 A1 | 3/2005 | Binette et al. |
| 2005/0100538 A1 | 5/2005 | Mohamed et al. |
| 2005/0112091 A1 | 5/2005 | DiMauro et al. |
| 2005/0282783 A1 | 12/2005 | Bujoli et al. |
| 2006/0210552 A1 | 9/2006 | Demopulos et al. |
| 2007/0237777 A1 | 10/2007 | DiMauro et al. |
| 2007/0269413 A1 | 11/2007 | Serhan et al. |
| 2008/0213261 A1 | 9/2008 | DiMauro et al. |
| 2009/0068270 A1 | 3/2009 | Attawia et al. |
| 2009/0155364 A1 | 6/2009 | Serhan et al. |
| 2009/0162351 A1 | 6/2009 | Brown et al. |
| 2009/0162376 A1 | 6/2009 | Brown et al. |
| 2009/0175943 A1 | 9/2009 | Attawia et al. |

FOREIGN PATENT DOCUMENTS

| | | |
|---|---|---|
| EP | 0 218 868 A2 | 4/1987 |
| EP | 0 288 088 B1 | 10/1988 |
| EP | 0 438 234 A1 | 7/1991 |
| EP | 0 950 417 A2 | 10/1999 |
| EP | 1 133 995 A2 | 9/2001 |
| EP | 1 153 607 A2 | 11/2001 |
| EP | 1 464 307 A1 | 10/2004 |
| WO | WO 91/02078 A1 | 2/1991 |
| WO | WO 92/07076 A1 | 4/1992 |
| WO | WO 92/16553 A1 | 10/1992 |
| WO | WO 93/16099 A2 | 8/1993 |
| WO | WO 97/28828 A1 | 8/1997 |
| WO | WO 98/24477 A1 | 6/1998 |
| WO | WO 99/45923 A1 | 9/1999 |
| WO | WO 2000/18409 | 4/2000 |
| WO | WO 2000/50079 | 8/2000 |
| WO | WO 01/85179 A2 | 11/2001 |
| WO | WO 02/057240 A1 | 7/2002 |
| WO | WO 02/100387 A1 | 12/2002 |
| WO | WO 2003/000190 A2 | 1/2003 |
| WO | WO 2004/022078 A1 | 3/2004 |
| WO | WO 2005/000283 A2 | 1/2005 |
| WO | WO 2005/011689 A2 | 2/2005 |
| WO | WO 2005/049055 A1 | 6/2005 |
| WO | WO 2005/053795 A2 | 6/2005 |
| WO | WO 2005/110276 A1 | 11/2005 |
| WO | WO 2006/031376 A2 | 3/2006 |

OTHER PUBLICATIONS

Andonopoulos, A., et al., "Intra-articular Anti-tumor Necrosis Factor α Antibody in Recalcitrant Arthritis of Behcet's Disease," *Clinical and Experimental Rheumatology*, 21(4 Suppl 30): S57-S58 (Jul.-Aug. 2003).

Aoki, Y., et al., "Local Application of Disc-related Cytokines on Spinal Nerve Roots," *Spine*, 27(15): 1614-1617 (2002).

Arai, I., et al., "Pretreatment with Loxoprofen Sodium, 6-OHDA or Anti TNF-alpha Antibody Reduce Fos-like Immunoreactivity in Rat Experimental Lumber Disc Herniation," 111, *Abstracts of the 30th Annual Meeting of the International Society for the Study of the Lumbar Spine*, Vancouver, Canada (May 2003).

Ariga, K., et al., "Mechanical Stress-induced Apoptosis of Endplate Chondrocytes in Organ-cultured Mouse Intervertebral Discs," *Spine*, 28(14): 1528-1533 (2003).

Ashkenazi, A., et al., "Protection Against Endotoxic Shock by a Tumor Necrosis Factor Receptor Immunoadhesin," *Proc. Natl. Acad. Sci. USA*, 88: 10535-10539 (1991).

Awasthi, Y., et al., "Purification and Properties of Human Erythrocyte Glutathione Peroxidase," *J.Biol. Chem.*, 250(13): 5144-5149 (1975).

Baker, D., et al., "Control of Established Experimental Allergic Encephalomyelitis by Inhibition of Tumor Necrosis Factor (TNF) Activity Within the Central Nervous System Using Monoclonal Antibodies and TNF Receptor-immunoglobulin Fusion Proteins," *Eur. J. Immunol.*, 24: 2040-2048 (1994).

Benjamin, L., et al., "A Plasticity Window for Blood Vessel Remodelling is Defined by Pericyte Coverage of the Preformed Endothelial Network and is Regulated by PDGF-B and VEGF," *Development*, 125: 1591-1598 (1998).

Biemond, P., et al., "Protective Factors Against Oxygen Free Radicals and Hydrogen Peroxide in Rheumatoid Arthritis Synovial Fluid," *Arthritis Rheum.*, 27(7): 760-765 (1984).

Biskobing, D., "Novel Therapies for Osteoporosis," *Expert Opinion Invest. Drugs*, 12(4): 611-621 (2003).

Boehm, J., et al., "New Inhibitors of p38 Kinase," *Exp. Opin, Ther. Patents*, 10(1): 25-37 (2000).

Bokarewa, M., et al., "Local Infusion of Infliximab for the Treatment of Acute Joint Inflammation," *Ann. Rheum Dis.*, 62: 783-784 (2003).

Braun, J., et al., "Anti-tumour Necrosis Factor α Therapy for Ankylosing Spondylitis: International Experience," *Ann. Rheum. Dis.*, 61(Supp. III): iii51-iii60 (2002).

Braun, J., et al., "Overview of the Use of the Anti-TNF Agent Infliximab in Chronic Inflammatory Diseases," *Expert Opin. Biol. Ther.*, 3(1): 141-168 (2003).

Bringman, T., et al., "Monoclonal Antibodies to Human Tumor Necrosis Factors Alpha and Beta: Application for Affinity Purification, Immunoassays, and as Structural Probes," *Hybridoma*, 6(5): 489-507 (1987).

Brown, K., et al., "Gelatin/Chondroitin 6-sulfate Microspheres for the Delivery of Therapeutic Proteins to the Joint," *Arthritis. & Rheum.*, 41(12): 2185-2195 (1998).

Burke, J., et al., "Human Nucleus Pulposus Secretes Transforming Growth Factor Beta-1 and Basic Fibroblast Growth Factor," 189, *Abstracts of the 30th Annual Meeting of the International Society for the Study of the Lumbar Spine*, Vancouver, Canada (May 2003).

Burke, J., et al., "Intervertebral Discs Which Cause Low Back Pain Secrete High Levels of Proinflammatory Mediators," *J. of Bone and Joint Surg.* [Br], 84-B: 196-201 (2002).

Butler, D., et al., "TNF Receptor Fusion Proteins are Effective Inhibitors of TNF-mediated Cytotoxicity on Human KYM-1D4 Rhabdomyosarcoma Cells," *Cytokine*, 6(6): 616-623 (1994).

Capon, D., et al., "Designing CD4 Immunoadhesins for AIDS Therapy," *Nature*, 337: 525-531 (1989).

Cardone, D., et al., "Diagnostic and Therapeutic Injection of the Hip and Knee," *Family Medicine*, 67(10): 2147-2152 (2003).

Castro, R., et al., "Failure of Bone Marrow Cells to Transdifferentiate Into Neural Cells in Vivo," *Science*, 297: 1299 (2002).

Čeponis, A., et al., "Effects of Low-dose, Noncytotoxic, Intraarticular Liposomal Clodronate on Development of Erosions and Proteoglycan Loss in Established Antigen-induced Arthritis in Rabbits," *Arthritis and Rheum.*, 44(8): 1908-1916 (2001).

Chae, H., et al., "The p38 Mitogen-activated Protein Kinase Pathway Regulates Interleukin-6 Synthesis in Response to Tumor Necrosis Factor in Osteoblasts," *Bone*, 28(1): 45-53 (2001).

Chan, J., et al., "Intraarticular Gene Transfer of TNFR:Fc Suppresses Experimental Arthritis with Reduced Systemic Distribution of the Gene Product," *Mol. Ther.*, 6(6): 727-736 (2002).

Cirillo, P., et al., "The Non-diaryl Heterocycle Classes of p38 MAP Kinase Inhibitors," *Current Topics in Medicinal Chemistry*, 2: 1021-1035 (2002).

CN 1 569 039 A (Niu X) Jan. 26, 2005 (abstract) World Patents Index [online]. London, GB: Derwent Publications, Ltd., Week 200577, Accession No. 2005-749289.

CN 1 647 808 A (Zhou C) Aug. 3, 2005 (abstract) World Patents Index [online]. London, GB: Derwent Publications, Ltd., Week 200621, Accession No. 2006-194507.

Connolly, J., et al., "Development of an Osteogenic Bone-marrow Preparation," *The Journal of Bone and Joint Surgery, Inc.*, 71-A(5): 684-691 (1989).

Conti, F., et al., "Successful Treatment with Intraarticular Infliximab for Resistant Knee Monarthritis in a Patient with Spondylarthropathy," *Arthritis & Rheumatism*, 52(4): 1224-1226 (2005).

Corcoran, A., et al., "Characterization of Ligand Binding by the Human p55 Tumour-necrosis-factor Receptor," *Eur. J. Biochem.*, 223: 831-840 (1994).

Cornefjord, M., et al., "Cerebrospinal Fluid Biomarkers in Experimental Spinal Nerve Root Injury," 38, *Abstracts of the 30th Annual Meeting of the International Society for the Study of the Lumbar Spine*, Vancouver, Canada (May 2003).

Crandall, C., "Combination Treatment of Osteoporosis: A Clinical Review," *J. of Women's Health &Gender-Based Medicine*, 11(3): 211-224 (2002).

Crevensten, G., et al., "Intervertebral Disc Cell Therapy for Regeneration: Mesenchymal Stem Cell Implantation in Rat Intervertebral Discs," *Ann. Biomed. Eng.*, 32(3): 430-434 (2004).

Dayer, J., "The Pivotal Role of Interleukin-1 in the Clinical Manifestations of Rheumatoid Arthritis," *Rheumatology*, Oxford University Press, London, GB, 42(Suppl 2): ii3-ii10 (2003).

Desai, S., et al., "Coated Microwell Plate-based Affinity Purification of Antigens," *Anal. Biochem.*, 328: 162-165 (2004).

DeSantis, A., et al., "Current and Emerging Therapies in Osteoporosis," *Expert Opin. Pharmacother.*, 3(7): 835-843 (2002).

Diwan, A., et al., "Current Concepts in Intervertebral Disk Restoration," *Tissue Engineering in Orthopedic Surgery*, 31(3): 453-464 (2000).

Edwards, S., et al., "Radiographic Assessment of Posterolateral Spine Fusion With and Without Platelet Rich Plasma," 117, *Abstracts of the 30th Annual Meeting of the International Society for the Study of the Lumbar Spine*, Vancouver, Canada (May 2003).

El-Khoury, G., et al., "Percutaneous Procedures for the Diagnosis and Treatment of Lower Back Pain: Diskography, Facet-joint Injection, and Epidural Injection," *AJR Am. J. Roentgenol.*, 157(4): 685-691 (1991).

Engelmann, H., et al., "Two Tumor Necrosis Factor-binding Proteins Purified From Human Urine," *J. Biol. Chem.*, 265(3): 1531-1536 (1990).

Eustice, C., et al., "What is Viscosupplementation?" [online] <http://arthritis.com/od/kneetreatments/g/viscosupplement_p.htm, Dec. 9, 2005>.

Ezra, A., et al., "Administration Routes and Delivery Systems of Bisphosphonates for the Treatment of Bone Resorption," *Adv. Drug Del. Rev.*, 42: 175-195 (2000).

Fendly, B., et al., "Murine Monoclonal Antibodies Defining Neutralizing Epitopes on Tumor Necrosis Factor," *Hybridoma*, 6: 359-370 (1987).

Földes, I., et al., "Trace Elements in Tissues of Normal and Vitamin $D_2$-treated Rats," *ACTA Biol. Acad. Sci. Hung.*, 26(3-4): 141-150 (1975).

Frain, J., et al., "Use of cDNA Microarrays to Investigate Cytokine Expression in Intervertebral Disc Degeneration," 126, *Abstracts of the 30th Annual Meeting of the International Society for the Study of the Lumbar Spine*, Vancouver, Canada (May 2003).

Gabay, C., "IL-1 Trap," *Curr. Opin. Invest. Drugs*, Curr. Drugs, London, GB, 4(5): 593-597 (2003).

Ganey, T., et al., "A Potential Role for Cell-based Therapeutics in the Treatment of Intervertebral Disc Herniation," *Eur. Spine J.*, 11(Suppl. 2): S206-S214 (2002).

Goodman, S., et al., "Effects of Local Infusion of TGFβ on Bone Ingrowth in Rabbit Chambers," *J. Biomed. Mat. Res. (Appl Biomater)*, 53: 475-479 (2000).

Gordon, J., et al., "Metalloproteinase Inhibitors as Therapeutics," *Clin. Exp. Rheumatol.*, 11(Suppl. 8): S91-S94 (1993).

Gori, A., et al., "Tumor Necrosis Factor-α Increased Production During Thalidomide Treatment in Patients With Tuberculosis and Human Immunodeficiency Virus Coinfection," *The Journal of Infectious Diseases*, 182: 639 (2000).

Goupille, P., et al., "Matrix Metalloproteinases: The Clue to Intervertebral Disc Degeneration?," *Spine*, 23(14): 1612-1626 (1998).

Guillen, C., et al., "The Effects of Local Administration of Lactoferrin on Inflammation in Murine Autoimmune and Infectious Arthritis," *Arthritis Rheum.*, 43(9): 2073-2080 (2000).

Haro, H., et al., "Matrix Metalloproteinase-7-dependent Release of Tumor Necrosis Factor-α in a Model of Herniated Disc Resorption," *J. Clin. Invest.*, 105(2): 143-150 (2000).

Hawks, D., "Alternative Medicine: Musculoskeletal System," *Clin. Tech. Small Anim. Pract.*, 17(1): 41-49 (2002).

Hayashida, K., et al., "Lactoferrin Enhances Peripheral Opioid-mediated Antinociception via Nitric Oxide in Rats," *Eur. J. Pharmacol.*, 484: 175-181 (2004).

Hayashida, K., et al., "Oral Administration of Lactoferrin Inhibits Inflammation and Nociception in Rat Adjuvant-induced Arthritis," *J. Vet. Med. Sci.*, 66(2): 149-154(2004).

Hirai, M., et al., "Production and Characterization of Monoclonal Antibodies to Human Tumor Necrosis Factor," *J. Immunol. Meth.*, 96: 57-62 (1987).

Hunter, C., et al., "Functional Behavior of Notochordal Cell Clusters in the Canine Nucleus Pulposus: Cell Communication and Survival," 70, *Abstracts of the 30th Annual Meeting of the International Society for the Study of the Lumbar Spine*, Vancouver, Canada (May 2003).

Hydrogels, Encyclopedia of Polymer Science and Technology, vol. 2, (Wiley and Sons, 2003).

Igarashi, A., et al., "Inflammatory Cytokines Release From Facet Joint Tissue in Degenerative Lumbar Disorders," 262, *Abstracts of the 30th Annual Meeting of the International Society for the Study of the Lumbar Spine*, Vancouver, Canada (May 2003).

Imai, Y., et al., "Effect of Recombinant Human Osteogenic Protein-1 on Extracellular Matrix Metabolism by Human Annulus Fibrosus and Nucleus Pulposus Cells," 205, *Abstracts of the 30th Annual Meeting of the International Society for the Study of the Lumbar Spine*, Vancouver, Canada (May 2003).

Imai, Y., et al., "The Quantification of Cytokine-induced Matrix Catabolism in Tissue Engeneered Intervertebral Discs," 67, *Abstracts of the 30th Annual Meeting of the International Society for the Study of the Lumbar Spine*, Vancouver, Canada (May 2003).

Inui, Y., et al., "Fas-ligand Expression on Nucleus Pulposus Cells Begins in Developing Embryo," 42, *Abstracts of the 30th Annual Meeting of the International Society for the Study of the Lumbar Spine*, Vancouver, Canada (May 2003).

Johnson, W., et al., "Collagenase Inhibitors: Their Design and Potential Therapeutic Use," *J. Enzyme Inhib.*, 2: 1-22 (1987).

Kamanh, A., et al., "Plasma Lipid Peroxidation and Antioxidant Levels in Patients with Rheumatoid Arthritis," *Cell Biochem. Funct.*, 22: 53-57 (2004).

Karppinen, J., et al., "Tumor Necrosis Factor-α Monoclonal Antibody, Infliximab, Used to Manage Severe Sciatica," *Spine*, 28(8): 750-754 (2003).

Kato, H., et al., "The Effect of IL-1 on the Rabbit Intervertebral Disc In Vivo," 199, *Abstracts of the 30th Annual Meeting of the International Society for the Study of the Lumbar Spine*, Vancouver, Canada (May 2003).

Kawakami, M., et al., "Possible Mechanism of Painful Radiculopathy in Lumbar Disc Herniation," *Clin. Orthop.*, 351: 241-251 (1998).

Kawakami, M., et al., "Role of IL-8, MCP-1 and PH in Neuropathic Pain Enhanced by Degenerative Nucleus Pulposus," 127, *Abstracts of the 30th Annual Meeting of the International Society for the Study of the Lumbar Spine*, Vancouver, Canada (May 2003).

Khot, A., et al., "The Use of Intradiscal Steroid Therapy for Lumbar Spinal Discogenic Pain—A Randomized Controlled Trial," *Spine*, 29(8): 833-837 (2004).

Kilic, B., et al., "Effects of Intra-articular Vitamin E and Corticosteroid Injection in Experimental Hemarthrosis in Rabbits," *Pediatr. Hematol. Oncol.*, 15(4): 339-346 (1998).

Kim, S., et al., "Ex Vivo Gene Delivery of IL-1Ra and Soluble TNF Receptor Confers a Distal Synergistic Therapeutic Effect in Antigen-induced Arthritis," *Mol. Ther.*, 6(5): 591-600 (2002).

Kimble, R., et al., "Estrogen Deficiency Increases the Ability of Stromal Cells to Support Murine Osteoclastogenesis Via an InterLeukin-1 and Tumor Necrosis Factor-mediated Stimulation of Macrophage Colony-stimulating Factor Production," *J. Biol. Chem.*, 271(46): 28890-28897 (1996).

Kimble, R., et al., "The Functional Block of TNF but Not of IL-6 Prevents Bone Loss in Ovariectomized Mice," *J. Bone Min. Res.*, 12(6): 935-941 (1997).

Koch, H., et al., "Spontaneous Secretion of Interleukin 1 Receptor Antagonist (IL-1Ra) by Cells Isolated from Herniated Lumbar Discal Tissue After Discectomy," *Cytokine*, 10(9): 703-705 (1998).

Kolls, J., et al., "Prolonged and Effective Blockade of Tumor Necrosis Factor Activity Through Adenovirus-mediated Gene Transfer," *Proc. Natl. Acad. Sci. USA*, 91: 215-219 (1994).

Korhonen, T., et al., "Efficacy of Infliximab for Disc Herniation-induced Sciatica One-year Follow-up," 14, *Abstracts of the 30th Annual Meeting of the International Society for the Study of the Lumbar Spine*, Vancouver, Canada (May 2003).

Kozbor, D., et al., "The Production of Monoclonal Antibodies from Human Lymphocytes," *Immunol. Today*, 4(3): 72-79 (1983).

Kurz, B., et al., "Dietary Vitamins and Selenium Diminish the Development of Mechanically Induced Osteoarthritis and Increase the Expression of Antioxidative Enzymes in the Knee Joint of STR/1N Mice," *Osteoarthritis Cartilage*, 10: 119-126 (2002).

Kwon, U., et al., "Dexamethasone Stimulates Cellular Proliferation While Downregulates Matrix Synthesis in Intervertebral Disc Cells," 29, *Abstracts of the 30th Annual Meeting of the International Society for the Study of the Lumbar Spine*, Vancouver, Canada (May 2003).

Lane, N., et al., "Basic Fibroblast Growth Factor Forms New Trabeculae that Physically Connect with Pre-existing Trabeculae, and This New Bone is Maintained With an Anti-resorptive Agent and Enhanced with an Anabolic Agent in an Osteopenic Rat Model," *Osteoporos. Int.*, 14: 374-382 (2003).

LaVan, D., et al., "Small-scale Systems for In Vivo Drug Delivery," *Nature Biotechnology*, 21(10): 1184-1191 (2003).

Le Maitre, C., et al., "Expression of the IL-1 Family in Human Intervertebral Disc," 217, *Abstracts of the 30th Annual Meeting of the International Society for the Study of the Lumbar Spine*, Vancouver, Canada (May 2003).

Le Maitre, C., et al., "Response of Human Intervertebral Disc Cells to IL-1," 216, *Abstracts of the 30th Annual Meeting of the International Society for the Study of the Lumbar Spine*, Vancouver, Canada (May 2003).

Le Visage, C., et al., "Interaction of Human Mescenchymal Stem Cells with Disc Cells: Changes in Biosynthesis of Extracellular Matrix," 25, *Abstracts of the 30th Annual Meeting of the International Society for the Study of the Lumbar Spine*, Vancouver, Canada (May 2003).

Lee, C., et al., "A Single Period of Hyperphysiologic Stretch Induces IL-6, TGF-beta and Cell Proliferation in Anulus Fibrosus Cells," 215, *Abstracts of the 30th Annual Meeting of the International Society for the Study of the Lumbar Spine*, Vancouver, Canada (May 2003).

Lee, J., et al., "Inhibition of p38 MAP Kinase as a Therapeutic Strategy," *Immunopharmacology*, 47: 185-201 (2000).

Lehman, T., et al., "Thalidomide Therapy for Recalcitrant Systemic Onset Juvenile Rheumatoid Arthritis," *J. Pediatrics*, 140: 125-7 (2002).

Lesslauer, W., et al., "Recombinant Soluble Tumor Necrosis Factor Receptor Proteins Protect Mice From Lipopolysaccharide-induced Lethality," *Eur. J. Immunol.*, 21: 2883-2886 (1991).

Li, J., et al., "The Effects of Bone Morphogenetic Protein 2 (BMP-2) and Cartilage-derived Morphogentic Protein 2 (CDMP-2) on Aggrecan Gene Expression in Chondrocytes," 30, *Abstracts of the 30th Annual Meeting of the International Society for the Study of the Lumbar Spine*, Vancouver, Canada (May 2003).

Liang, C., et al., "Production and Characterization of Monoclonal Antibodies Against Recombinant Human Tumor Necrosis Factor/Cachectin," *Biochem. Biophys. Res. Comm.*, 137: 847-854 (1986).

Loetscher, H., et al., "Molecular Cloning and Expression of the Human 55 kd Tumor Necrosis Factor Receptor," *Cell*, 61: 351-359 (1990).

Lotz, J., et al., "Cytokines in Normal, Degenerated, and Nucleoplasty-treated Porcine Discs," 157, *Abstracts of the 30th Annual Meeting of the International Society for the Study of the Lumbar Spine*, Vancouver, Canada (May 2003).

Lubberts, E., et al., "Intra-articular IL-10 Gene Transfer Regulates the Expression of Collagen-induced Arthritis (CIA) in the Knee and Ipsilateral Paw," *Clin. Exp. Immunol.*, 120: 375-383 (2000).

Maddipati, K., et al., "Characterization of the Major Hydroperoxide-reducing Activity of Human Plasma," *J. Biol. Chem.*, 262(36): 17398-17403 (1987).

Maeda, S., et al., "Changes With Age in Proteoglycan Synthesis in Cells Cultured In Vitro From the Inner and Outer Rabbit Annulus Fibrosus," *Spine*, 25(2): 166-169 (2000).

Marriott, J., et al., "CC-3052: A Water-soluble Analog of Thalidomide and Potent Inhibitor of Activation-induced TNF-α Production," *J. Immunol.*, 161: 4236-4243 (1998).

Martinez, J., et al., "Blood Platelet Glutathione Peroxidase: Some Properties and Partial Purification," *Thromb. Res.*, 19: 73-83 (1980).

McMillan, D., et al., "Intra-operative Autologous Blood Management," *Transfusion and Apheresis Science*, 27(1): 73-81 (2002).

Meager, A., et al., "Preparation and Characterization of Monoclonal Antibodies Directed Against Antigenic Determinants of Recombinant Human Tumour Necrosis Factor (rTNF)," *Hybridoma*, 6(3): 305-311 (1987).

Meijer, H., et al., "The Production of Anti-inflammatory Cytokines in Whole Blood by Physico-chemical Induction," *Inflamm. Res.*, 52: 404-407 (2003).

Miyamoto, H., et al., "The Effect of Mechanical Stress on the Production of Inflammatory Agents by Disc Cells," 110, *Abstracts of the 30th Annual Meeting of the International Society for the Study of the Lumbar Spine*, Vancouver, Canada (May 2003).

Möer, A., et al., "Monoclonal Antibodies to Human Tumor Necrosis Factor: In Vitro and In Vivo Application," *Cytokine*, 2(3): 162-169 (1990).

Molloy, T., et al., "The Roles of Growth Factors in Tendon and Ligament Healing," *Sports Med.*, 33(5): 381-394 (2003).

Moreira, A., et al., "Thalidomide Exerts Its Inhibitory Action on Tumor Necrosis Factor α by Enhancing mRNA Degradation," *J. Exp. Med.*, 177: 1675-1680 (1993).

Moroney, P., "PH and Anti-inflammatory Agents Modulate Nucleus Pulposus Cytokine Secretion," *The Spine Journal*, 2(5 Suppl): 49S-50S (2002) (abstract).

Muller, G., et al., "Amino-substituted Thalidomide Analogs: Potent Inhibitors of TNF-α Production," *Bioorg. Med. Chem. Lett.*, 9: 1625-1630 (1999).

Müller, R., "Determination of Affinity and Specificity of Anti-hapten Antibodies by Competitive Radioimmunoassay," *Meth. Enzymol.*, 92: 589-601 (1983).

Nakamura, K., et al., "Local Application of Basic Fibroblast Growth Factor into the Bone Increases Bone Mass at the Applied Site in Rabbits," *Arch. Orthop. Trauma Surg.*, 115: 344-346 (1996).

Nakamura, K., et al., "Stimulation of Endosteal Bone Formation by Local Intraosseous Application of Basic Fibroblast Growth Factor in Rats," *Rev. Rhum.* [Engl. Ed.], 64(2): 101-105 (1997).

Niccoli, L., et al., "Intraarticular Injection of Infliximab in Relapsing Knee Effusion in Psoriatic Arthritis: A Pilot Study," *Ann. Rheum. Dis.*, 62(1): 239-240 (2003) and EULAR—Annual European Congress of Rheumatology, Lisbon, Portugal (2003) (abstract).

Nikas, S., et al., "Treatment of Resistant Rheumatoid Arthritis by Intra-articular Infliximab Injections: A Pilot Study," *Ann Rheum Dis.*, 63: 102-103 (2004).

Nikas, S., et al., "Treatment of Resistant Rheumatoid Arthritis by Intra-articular Injections with Infliximab: A Pilot Study," *Ann. Rheum. Dis.*, 62(1): 408 (2003) and EULAR—Annual European Congress of Rheumatology, Lisbon, Portugal (2003) (abstract).

Ohno, K., et al., "Transdiscal Lumbar Sympathetic Block: A New Technique for a Chemical Sympathectomy," *Anesth. Analg.*, 85: 1312-1316 (1997).

Ohtori, S., et al., "TNF-α and TNF-α Receptor 1 Upregulation in GLIA and Neurons After Nerve Injury. Studies in Murine DRG and Spinal Cord," 13, *Abstracts of the 30th Annual Meeting of the International Society for the Study of the Lumbar Spine*, Vancouver, Canada (May 2003).

Ohtori, S., et al., "TNF-α-Deficient Mice Have Fewer Macrophages in Injured Nerve and Reduced Glial Activation in DRG and Spinal Cord," 250, *Abstracts of the 30th Annual Meeting of the International Society for the Study of the Lumbar Spine*, Vancouver, Canada (May 2003).

Okuma, M., et al., "Rotary Cell Culture System Stimulates Annulus Fibrosus Cell Proliferation but Suppresses Proteoglycan Metabolism," 164, *Abstracts of the 30th Annual Meeting of the International Society for the Study of the Lumbar Spine*, Vancouver, Canada (May 2003).

Olmarker, K., et al., "Selective Inhibition of Tumor Necrosis Factor-α Prevents Nucleus Pulposus-induced Thrombus Formation, Intraneural Edema, and Reduction of Nerve Conduction Velocity," *Spine*, 26(8): 863-869 (2001).

Pacifici, R., "Editorial: Cytokines, Estrogen, and Postmenopausal Osteoporosis—The Second Decade," *Endocrinology*, 139(6): 2659-2661 (1998).

Pargellis, C., et al., "Inhibition of p38 MAP Kinase by Utilizing a Novel Allosteric Binding Site," *Nature Structural Biology*, 9(4): 268-272 (2002).

Pederson, A., et al., "Thermal Assembly of a Biomimetic Mineral/Collagen Composite," *Biomaterials*, 24: 4881-4890 (2003).

Peppel, K., et al., "A Tumor Necrosis Factor (TNF) Receptor-IgG Heavy Chain Chimeric Protein as a Bivalent Antagonist of TNF Activity," *J. Exp. Med.*, 174: 1483-1489 (1991).

Raucci, A., et al., "Activation of the ERK1/2 and p38 Mitogen-activated Protein Kinase Pathways Mediates Fibroblast Growth Factor-induced Growth Arrest of Chondrocytes," *J. Biol. Chem.*, 279(3): 1747-1756 (2004).

Richardson, S., et al., "Human Bone Marrow Mesenchymal Stromal Cells as a Source of Chondrocytes for Treatment of Intervertebral Disc Degeneration," 27, *Abstracts of the 30th Annual Meeting of the International Society for the Study of the Lumbar Spine*, Vancouver, Canada (May 2003).

Risbud, M., et al., "Mesenchymal Stem Cells Respond to Their Microenvironment In Vitro to Assume Nucleus Pulposus-like Phenotype," 26, *Abstracts of the 30th Annual Meeting of the International Society for the Study of the Lumbar Spine*, Vancouver, Canada (May 2003).

Rodan, G., et al., "Therapeutic Approaches to Bone Diseases," *Science*, 289: 1508-1514 (2000).

Sakai, D., et al., "Autologous Transplantation of Mesenchymal Stem Cells for Disc Repair," 24, *Abstracts of the 30th Annual Meeting of the International Society for the Study of the Lumbar Spine*, Vancouver, Canada (May 2003).

Sakai, D., et al., "Transplantation of Mesenchymal Stem Cells Embedded in Atelocollagen® Gel to the Intervertebral Disc: A Potential Therapeutic Model for Disc Degeneration," *Biomaterials*, 24: 3531-3541 (2003).

Salin, M., et al., "Free Radicals and Inflammation: Protection of Phagocytosing Leukocytes by Superoxide Dismutase," *J. Clin. Invest.*, 56: 1319-1323 (1975).

Sampaio, E., et al., "Thalidomide Selectively Inhibits Tumor Necrosis Factor α Production by Stimulated Human Monocytes," *J. Exp. Med.*, 173: 699-703 (1991).

Schalkwijk, J., et al., "Cationization of Catalase, Peroxidase, and Superoxide Dismutase," *J. Clin. Invest.*, 76: 198-205 (1985).

Schall, T., et al., "Molecular Cloning and Expression of a Receptor for Human Tumor Necrosis Factor," *Cell*, 61: 361-370 (1990).

Schatteman, L., et al., "Treatment of Refractory Inflammatory Monoarthritis in Ankylosing Spondylitis by Intraarticular Injection of Infliximab," *The Journal of Rheumatology*, 33: 182-85 (2006).

Shiel, W., "Ankylosing Spondylitis," MedicineNet.com [online], Sep. 2005 [retrieved on Jun. 20, 2006]. Retrieved from the Internet <URL: http://www.medicinenet.com/script/main/art.asp?articlekey=274&pf=3&page=2>.

Sobajima, S., et al., "Stem Cell Therapy for Degenerative Disc Disease: An In-vitro Feasibility Study," 43, *Abstracts of the 30th Annual Meeting of the International Society for the Study of the Lumbar Spine*, Vancouver, Canada (May 2003).

Steer, J., et al., "Altered Leucocyte Trafficking and Suppressed Tumour Necrosis Factor α Release from Peripheral Blood Monocytes After Intra-articular Glucocorticoid Treatment," *Ann. Rheum. Dis.*, 57(12): 732-737 (1998).

Stepanik, T., et al., "Coisolation of Glutathione Peroxidase, Catalase and Superoxide Dismutase From Human Erythrocytes," *J. Biochem. Biophys. Methods*, 20: 157-169 (1990).

Stern, S., et al., "Human Intervertebral Disc Cell Culture for Disc Disorders," *Clin. Orthop.*, 419: 238-244 (2004).

Takada, T., et al., "IL-6 Production was Upregulated by Interaction Between Disc Tissue and Macrophages," 41, *Abstracts of the 30th Annual Meeting of the International Society for the Study of the Lumbar Spine*, Vancouver, Canada (May 2003).

Takegami, K., et al., "Osteogenic Protein-1 Enhances Matrix Replenishment by Intervertebral Disc Cells Previously Exposed to Interleukin-1," *Spine*, 27(12): 1318-1325 (2002).

Tanny, G., et al., "Improved Filtration Technique for Concentrating and Harvesting Bacteria," *Appl. Environ. Microbiol.*, 40(2): 269-273 (1980).

Teo, S., "Properties of Thalidomide and its Analogues: Implications for Anticancer Therapy," *AAPS Journal*, 7(1): E14-E19 (2005).

Tiku, M., et al., "Aggrecan Degradation in Chondrocytes is Mediated by Reactive Oxygen Species and Protected by Antioxidants," *Free Radic. Res.*, 30: 395-405 (1999).

Tiku, M., et al., "Evidence Linking Chondrocyte Lipid Peroxidation to Cartilage Matrix Protein Degradation," *J. Biol. Chem.*, 275(26): 20069-20076 (2000).

Tobinick, E., et al., "Perispinal TNF-alpha Inhibition for Discogenic Pain," *Swiss Med. Wkly.*, 133: 170-177 (2003).

Tobinick, E., "Targeted Etanercept for Discogenic Neck Pain: Uncontrolled, Open-label Results in Two Adults," *Clin. Thera.*, 25(4): 1211-1218 (2003).

Tobinick, E., "Targeted Etanercept for Treatment-refractory Pain Due to Bone Metastasis: Two Case Reports," *Clinical Therapeutics.*, 25(8): 2279-2288 (2003).

Tracey, K., et al., "Tumor Necrosis Factor in Metabolism of Disease: Hormonal Actions Versus Local Tissue Effects," *Nouv. Rev. Fr. Hematol.*, 34 Suppl: S37-42 (1992) (abstract).

Trif, M., et al., "Liposomes as Possible Carriers for Lactoferrin in the Local Treatment of Inflammatory Diseases," *Exp. Biol. Med.*, 226(6): 559-564 (2001).

Tsuji, T., et al., "Age-Related Changes in M-RNA Expression of Various Regulatory Factors in Rabbit Intervertebral Disc," 81, *Abstracts of the 30th Annual Meeting of the International Society for the Study of the Lumbar Spine*, Vancouver, Canada (May 2003).

Vahle, J., et al., "Skeletal Changes in Rats Given Daily Subcutaneous Injections of Recombinant Human Parathyroid Hormone (1-34) for 2 Years and Relevance to Human Safety," *Toxicol. Pathol.*, 30(3): 312-321 (2002).

Vukicevic, S., et al., "Induction of Nephrogenic Mesenchyme by Osteogenic Protein 1 (Bone Morphogenetic Protein 7)," *Proc. Natl. Acad. Sci.*, 93: 9021-9026 (1996).

Weiler, C., et al., "Expression of TNF-α in Autopsy and Biopsy Specimens of Intervertebral Discs of Various Age and Degeneration," 233, *Abstracts of the 30th Annual Meeting of the International Society for the Study of the Lumbar Spine*, Vancouver, Canada (May 2003).

Williams, A., et al., "Amelioration of Rat Antigen-induced Arthritis by Liposomally Conjugated Methotrexate is Accompanied by Down-regulation of Cytokine mRNA Expression," *Rheumatology*, 40: 375-383 (2001).

Wittenberg, R., et al., "In Vitro Release of Prostaglandins and Leukotrienes from Synovial Tissue, Cartilage, and Bone in Degenerative Joint Diseases," *Arthritis & Rheumatism*, 36(10): 1444-1450 (Oct. 1993).

Xie, X., et al, "Treatment of Spondylodiscitis Intravenous Versus Percutaneous Intradiscal Applications of Antibiotics: An Experimental Study in Rabbits," 120, *Abstracts of the 30th Annual Meeting of the International Society for the Study of the Lumbar Spine*, Vancouver, Canada (May 2003).

Yabuki, S., et al., "Prevention of Compartment Syndrome in Dorsal Root Ganglia Caused by Exposure to Nucleus Pulposus," *Spine*, 26(8): 870-875 (2001).

Yaffe, A., et al., "Combined Local Application of Tetracycline and Bisphosphonate Reduces Alveolar Bone Resorption in Rats," *J. Periodontol.*, 74(7): 1038-1042 (2003).

Yang, J., et al., "Purification and Quantitation of a Rat Plasma Selenoprotein Distinct from Glutathione Peroxidase Using Monoclonal Antibodies," *J. Biol. Chem.*, 262(27): 13372-13375 (1987).

Yoon, S., et al., "LMP-1 Upregulates Proteoglycan Synthesis in Intervertebral Disc Cells Through a BMP Mediated Process," 31,

*Abstracts of the 30th Annual Meeting of the International Society for the Study of the Lumbar Spine*, Vancouver, Canada (May 2003).

Zhang, C., et al., "Mitogen-activated Protein (MAP) Kinase Regulates Production of Tumor Necrosis Factor-α and Release of Arachidonic Acid in Mast Cells," *J. Biol. Chem.*, 272(20): 13397-13402 (1997).

Ando, N., et al., "An Immunohistochemical Study of the Degenerative Lumbar Disc," Orthopedics & Traumatology 44(1): 176-178 (1995) (Published in Japanese with English Abstract).

Blight, A.R., "Miracles and molecules—progress in spinal cord repair," Nature Neuroscience Supplement 5:1051-1054 (Nov., 2002).

www.medicinenet.com, downloaded, Jun. 20, 2006.

Yorimitsu, E., "A Comparative Study on the Pathological Changes of Intervertebral Discs after Intradiscal Injection of Various Kinds of Steroid Materials: An Experimental Study," Journal Keio Medical Society 74(5): 303-315 (1997) (Published in Japanese with English Abstract).

* cited by examiner

TRANSDISCAL ADMINISTRATION OF CYCLINE COMPOUNDS

RELATED APPLICATIONS

This application is a divisional of U.S. application Ser. No. 10/640,412, filed Aug. 13, 2003 now U.S. Pat. No. 7,553,827. The entire teachings of the above application are incorporated herein by reference.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus with its cushioning qualities. These nucleus pulposus cells may also secrete small amounts of cytokines as well as matrix metalloproteinases (MMPs). The cytokines help regulate the metabolism of the nucleus pulposus cells.

In some instances of disc degeneration disease (DDD), gradual degeneration of the intervertebral disc is caused by mechanical instabilities in other portions of the spine. In these instances, increased or unconventional loads and pressures on the nucleus pulposus cause the cells to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins which leads to nerve irritation and pain.

As DDD progresses, the toxic levels of the cytokines present in the nucleus pulposus begin to degrade the extracellular matrix. In particular, the MPPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, and thereby typically upregulating MMPs. As this destructive cascade continues and DDD further progresses, the disc begins to bulge ("a herniated disc"), and then ultimately ruptures, causing the nucleus pulposus to contact the spinal cord and produce pain.

Olmarker, *Spine,* 26(8): 863-9 (2001) ("Olmarker I") and Aoki, *Spine,* 27(15): 1614-17 (2002) teach that TNF-α (TNF-alpha) appears to play a role in producing the pain associated with the nucleus pulposus contacting nerve roots of the spinal cord. Olmarker discourages the use of non-specific TNF-α inhibitors in spine-related drug therapies, and particularly those that have anti-biotic effects.

U.S. Published Patent Application No. U.S. 2003/0039651 ("Olmarker II") teaches a therapeutic treatment of nerve disorders comprising administration of a therapeutically effective dosage of a number of drugs, including cycline compounds. According to Olmarker, tetracycline are non-specific inhibitors of TNF-α.

In the examples of Olmarker II, Olmarker II further teaches that these drugs are to be administered through systemic pathways. In particular, Olmarker II teaches that "the major contribution of TNF-α may be derived from recruited, aggregated and maybe even extravasated leukocytes, and that successful pharmacologic block may be achieved only by systemic treatment. Of note, Olmarker II appears to discourage the local addition of doxycycline to an autotransplanted nucleus pulposus to be applied to a spinal cord.

PCT Published Patent Application No. WO 02/100387 ("Olmarker III") teaches the prevention of neovasculariation and/or neo-innervation of intervertebral discs by the administration of anti-angiogenic substances. Again, however, Olmarker III teaches systemic administration of these therapeutic agents.

U.S. Pat. No. 6,419,944 ("Tobinick") discloses treating herniated discs with cytokine antagonists, including infliximab. However, Tobinick teaches that local administration involves a subcutaneous injection near the spinal cord. Accordingly, Tobinick does not teach a procedure involving a sustained delivery of a drug for the treatment of DDD, nor directly administering a cycline compound into the disc.

U.S. Published Patent Application No. 2003/0049256 ("Tobinick II") discloses that injection of such therapeutic molecules to the anatomic area adjacent to the spine is accomplished by interspinous injection, and preferably is accomplished by injection through the skin in the anatomic area between two adjacent spinous processes of the vertebral column.

Tobinick, *Swiss Med. Weekly,* 133:170-77 (2003) ("Tobinick III") teaches perispinal and epidural administration of specific TNF-α inhibitors.

Karppinen, *Spine,* 28(8): 750-4 (2003), teaches intravenously injecting or orally administering infliximab into patients suffering from sciatica.

As with Tobinick I and II, Karppinen does not teach a procedure involving a sustained delivery of a drug for the treatment of DDD, nor directly administering a cycline compound into the disc.

U.S. Pat. No. 6,352,557 (Ferree) teaches adding therapeutic substances such as anti-inflammatory medications to morselized extra-cellular matrix, and injecting that combination into an intervertebral disc.

Alini, *Eur. Spine J.,* 11(Supp.2):S215-220 (2002) teaches therapies for early stage DDD, including injection of inhibitors of proteolytic enzymes or biological factors that stimulate cell metabolic activity (i.e., growth factors) in order to slow down the degenerative process. "Inhibitors of proteolytic enzymes" constitutes a broad class of compounds, including a) inhibitors of proteolytic enzyme synthesis and b) inhibitors of proteolytic enzyme activity.

U.S. Published Patent Application U.S. 2002/0026244 ("Trieu") discloses an intervertebral disc nucleus comprising a hydrogel that may deliver desired pharmacological agents. Trieu teaches that these pharmacological agents may include growth factors such as TGF-β (TGF-beta) and anti-inflammatory drugs, including steroids. Trieu further teaches that these pharmacological agents may be dispersed within the hydrogel having an appropriate level of porosity to release the pharmacological agent at a desired rate. Trieu teaches that these agents may be released upon cyclic loading or upon resorption.

Goupille, *Spine,* 23(14): 1612-1626 (1998) identifies tetracycline as an inhibitor of MMP activity. However, Goupille also identifies corticosteroids, retinoic acid, TGF-β, PGE1 and PGE2 as inhibitors of MMP synthesis; identifies α2-macroglobulin, hydroxamic acid, derivatives, tetracycline and quinolones as inhibitors of MMP activity; and identifies bFGF, EGF, Retenoic acid, TGF-β, IL-6, IL-1 LIF, dexamethasone, phorbol ester, and synthetic Vitamin A analogs as stimulators of Tissue Inhibitors of metalloproteinases ("TIMPs"). Moreover, as to administration route, Goupille explicitly identifies only the oral administration route.

In sum, although investigators have generally taught the transdiscal administration of inhibitors of proteolytic enzymes, when investigators have specifically identified the administration of a cycline compound for spine-related therapy, the investigators appear to teach only the administration of the cycline compound to tissue outside the disc. Moreover, Olmarker II appears to discourage the administration of a cycline compound to a nucleus pulposus.

SUMMARY OF THE INVENTION

The present inventors have developed a number of procedures for efficaciously treating degenerative disc disease by drug therapy.

In accordance with the present invention, the present inventors have developed a method of treating an intervertebral disc in which a cycline compound is administered transdiscally. The target tissue is a degenerating disc.

There are several advantages to directly administering a cycline compound transdiscally:

First, cycline compounds inhibit the activity of MMPs. Since it is known that MMPs play primary roles in the degradation of the extracellular matrix (ECM) of the nucleus pulposus, injecting a cycline compound directly into the disc in a therapeutically effective amount can prevent the MMPs located in the disc from causing or inducing any further ECM degradation. In effect, the transdiscal administration of the cycline compound helps arrest the aging process of the degenerative disc. Accordingly, the present invention seeks to treat the degenerative disc at a much earlier stage of DDD than Olmarker, and thereby prevents degradation of the ECM.

Second, cycline compounds also inhibit the activity of TNF-α. There are nerve ending nociceptors within the annulus fibrosus, and TNF-α participates in the irritation of such nerves. Injecting a cycline compound into the disc space in a therapeutically effective amount can prevent the TNF-α from causing nerve irritation within the disc. Thus, the pain attributed to irritation of these nerves can be effectively eliminated by transdiscal administration of cycline compounds.

Third, since the annulus fibrosus portion of the disc comprises a dense fibrosus structure, this outer component of the disc may provide a suitable depot for the cycline compound, thereby increasing its half-life in the disc.

Fourth, since at least MMPs may be secreted by at least one of invading macrophages, nucleus pulposus cells or annulus fibrosus cells, transdiscal injection of the cycline compound will advantageously attack the MMPs at their source of origination.

Accordingly, in a first aspect of the present invention, there is provided a method of treating degenerative disc disease in an intervertebral disc having a nucleus pulposus, comprising transdiscally administering an effective amount of a formulation comprising a cycline compound into the intervertebral disc.

DETAILED DESCRIPTION OF THE INVENTION

For the purposes of the present invention, the terms "inhibitor" and "antagonist" are used interchangeably. A cytokine or MMP may be inhibited at the synthesis level, at the translation level, by shedding, by antibodies, or by soluble receptors. The term "patient" refers to a human having a degenerating disc.

For the purposes of the present invention, "transdiscal administration" includes, but is not limited to:
 a) injecting a formulation into the nucleus pulposus of a degenerating disc, such as a relatively intact degenerating disc;
 b) injecting a formulation into the annulus fibrosus of a degenerating disc, such as a relatively intact degenerating disc;
 c) providing a formulation in a patch attached to an outer wall of the annulus fibrosus,
 d) providing a formulation in a depot at a location outside but closely adjacent to an outer wall of the annulus fibrosus (hereinafter, "trans-annular administration"); and
 e) providing the formulation in a depot at a location outside but closely adjacent to an endplate of an adjacent vertebral body (hereinafter, "trans-endplate administration").

Because DDD is a continuous process, the degenerating disc to which the therapeutic drug is administered may be in any one of a number of degenerative states. Accordingly, the degenerating disc may be an intact disc. The degenerating disc may be a herniated disc (wherein a portion of the annulus fibrosus has a bulge). The degenerating disc may be a ruptured disc (wherein the annulus fibrosus has ruptured and bulk nucleus pulposus has exuded). The degenerating disc may be delaminated (wherein adjacent layers of the annulus fibrosus have separated). The degenerating disc may have fissures (wherein the annulus fibrosus has fine cracks or tears through which selected molecules from the nucleus pulposus can leak).

The present invention is directed to providing a cycline compound directly to (e.g., through) a diseased intervertebral disc. In one embodiment, the cycline compound is administered in an amount effective to inhibit the action of a pro-inflammatory cytokine (such as TNF-α) or a matrix metalloproteinase (MMP). These cytokines can be present in the nucleus pulposus. In one embodiment, the cycline compound is administered in an amount effective to inhibit the action of an MMP released by disc cells during the degenerative process. In one embodiment, the cycline compound is administered in an amount effective to both a) inhibit a specific pro-inflammatory cytokine (such as TNF-α), and b) inhibit an ECM-degrading MMP released by local cells during the degenerative process. In one embodiment, the cycline compound is administered in an amount to inhibit TNF-α and thereby reduce pain and/or arrest degradation of the cellular matrix. In one embodiment, the cycline compound is administered in an amount to inhibit an MMP and thereby arrest degradation of the ECM.

In some embodiments, the cycline compound is selected from the group consisting of doxycycline, lymecycline, oxicycline compound, tetracycline, minocycline, chemically modified tetracycline (CMT) and KB-R7785. Preferably, doxycycline or minocycline is selected.

Cycline compounds inhibit TNF-α in a non-specific manner. TNF-α and other similar bioactive substances are first produced in an inactive form and transported to the cell membrane. Upon activation, the active part of the pro-TNF-α is cleaved and released. This process is called shedding and may be initiated by one or more enzymes. These enzymes all have in common a metal ion and are called matrix metalloproteinases (MMPs). Cycline compounds are known to bind to metal ions and will thereby inhibit the action of the MMP and subsequently the release of TNF-α and other pro-inflammatory cytokines in a non-specific manner.

DDD involves the progressive degeneration of a disc in which many factors are involved. In many instances, simply providing a single dose or even a regimen over the space of a few days may not be sufficient to resolve the DDD. For example, if DDD were caused in part by, for example, mechanical instability in a functional spinal unit, then simply providing a one-time therapy for the transdiscal cells would likely only delay the onset of the DDD. Therefore, there is a need to provide a long-term drug therapy treatment of DDD that does not require multiple injections.

Because it is believed that some of the cytokines of interest both produce pain and degrade the ECM when present within the nucleus pulposus, it is desirable for the cycline compound to remain within the nucleus pulposus as long as possible in a pharmaceutically effective amount. The half-life of the cycline compound within the nucleus pulposus will depend upon many factors, including the size of the cycline compound and its charge. In general, the larger the molecular weight of the cycline compound, the more likely it is to remain contained by the annulus fibrosus portion of the disc.

If a cycline compound with a relatively short half-life is selected, then it would be desirable for a relatively large dose of the cycline compound to be administered into the disc. In this condition, quick depletion of the cycline compound would not cause the cycline compound to fall below therapeutically effective levels until an extended period of time has elapsed.

Although a large dose of the cycline compound would be desirable in some instances, injecting a critical volume of water can increase pressure in the nucleus pulposus. Nociceptors present on the inner wall of the annulus fibrosus react to this increased pressure and produce pain. In some cases, the added amount could be as little as one cc by volume to produce pain. Accordingly, if a dilute concentration of a cycline compound is added to the nucleus pulposus to provide a large dose, the resulting pressure increase caused by this added volume could be sufficient to cause acute pain.

For example, if it were determined that about 2 mg of a cycline compound was needed to therapeutically affect a nucleus pulposus, and that cycline compound was provided in concentrations of about 2 mg/ml, then at least about 1 ml of the cycline compound would need to be injected into the nucleus pulposus in order to provide the desired therapeutic effect. However, when injecting volumes into the nucleus pulposus, it is desirable that the volume of drug delivered be less than 1 ml, preferably no more than 0.5 ml, more preferably between about 0.03 ml and about 0.3 ml. When injected in these smaller quantities, it is believed the added volume will not cause an appreciable pressure increase in the nucleus pulposus.

Accordingly, in some embodiments, the concentration of the cycline compound in the administered drug, i.e., formulation, (i.e., sustained delivery device) is at least about 20 mg/ml. In this condition, no more than 0.1 ml of the drug need be injected. Preferably, the concentration of the cycline compound in the administered drug is at least 50 mg/ml. In this condition, no more than about 0.05 ml (i.e., a maximum of 0.05 ml) of the drug need be injected. In one embodiment, the concentration of cycline compound in the formulation is less than about 100 mg/ml.

In some embodiments, the cycline compound is provided in a sustained release device (i.e., sustained delivery device). The administration formulation can comprise the sustained release device. The sustained release device is adapted to remain within the disc for a prolonged period and slowly release the cycline compound contained therein to the surrounding environment. This mode of delivery allows the cycline compound to remain in therapeutically effective amounts within the disc for a prolonged period. One or more additional therapeutic agents can also be delivered by a sustained delivery device.

In some embodiments, a formulation comprising a sustained release device is provided closely adjacent to the outer wall of the annulus fibrosis. In some embodiments, the sustained release device comprises a bioresorbable material whose gradual erosion causes the gradual release of the cycline compound to the disc environment. In some embodiments, the sustained release device comprises a bioresorbable polymer. In some embodiments, the bioresorbable polymer has a half-life of at least about one month, for example, at least two months, e.g., at least 6 months.

In some embodiments, the cycline compound is predominantly released from the sustained delivery device by its diffusion through the sustained delivery device (preferably, though a polymer or a porous ceramic such as hydroxyapatite. In others, the cycline compound is predominantly released from the sustained delivery device by the biodegradation of the sustained delivery device (preferably, biodegradation of a polymer or a porous ceramic such as hydroxyapatite).

In some embodiments, the sustained release device provides controlled release. In others, it provides continuous release. In others, it provides intermittent release. In others, the sustained release device comprises a biosensor. Other release modes may also be used.

In some embodiments, the sustained delivery device comprises bioerodable macrospheres. The cycline compound is preferably contained in a gelatin (or water or other solvent) within the capsule, and is released to the disc environment when the outer shell has been eroded. The device can include a plurality of capsules having outer shells of varying thickness, so that the sequential breakdown of the outer shells provides periodic release of the cycline compound.

In some embodiments, the sustained delivery device comprises an inflammatory-responsive delivery system, such as one comprising bioerodable microspheres that are eroded by invading macrophages. This technology provides a high correspondence between physiologic inflammation of disc environment and the release of the cycline compounds into that environment. In one embodiment, the technology disclosed in Brown et al., *Arthritis. Rheum.*, 41(12): 2185-95 (December 1998) is selected.

In some embodiments, the sustained delivery device comprises a device disclosed in U.S. Pat. No. 5,728,396 ("Peery"), which is incorporated by reference in its entirety.

In some embodiments, the sustained delivery device comprises a liposomal delivery system, such as that disclosed in WO 03/000190. Liposomes are small spheres whose walls are layers of lipids with water. As they form, liposomes entrap water and any water soluble solutes that are present. Because of this entrapping ability, they are useful as delivery systems. For the purposes of the present invention, a preferred embodiment includes the use of a multilamellar vesicle, and any naturally occurring phospholipid, such as dipalmitoylphosphatidylcholine (DPPC).

A liposome may be a vesicle having at least one lipid bilayer surrounding an inner liquid phase (a lipid bilayer surrounding either a liquid core or a liquid phase dispersed between it and another lipid bilayer). The liposome may have various structures such as multilamellar (MLVs), unilamellar (ULVs) and paucilamellar (PLVs) vesicles. The resulting structure of the liposome is dependent, in part, on the choice of materials forming the hydrophobic phase and the manufacturing parameters, such as temperature and incubation time.

Some liposomes comprise at least one amphiphilic bilayer-forming substance. The therapeutic substances contained therein may be contained either within the lipid bilayer or the hydrophilic compartments of the liposome. The amphiphilic bilayer-forming substance comprises both a hydrophilic and a lipophilic group and is capable of forming, either alone or in combination with other lipids, the bilayer of a liposome. The lipid can have single or multiple lipophilic side chains being either saturated or unsaturated in nature and branched or linear in structure. The amphiphilic bilayer-forming substance can be a phosphoholipid or a ceramide.

In some embodiments, the sustained delivery device comprises a plurality (e.g., at least one hundred) of water-containing chambers, each chamber containing a cycline compound. Each chamber is defined by bilayer lipid membranes comprising synthetic duplicates of naturally occurring lipids. The release of the drug can be controlled by varying at least one of the aqueous excipients, the lipid components, and the manufacturing parameters. Preferably, the formulation comprises no more than 10% lipid. In some embodiments, the DEPOFOAM™ technology of Skyepharma PLC (London, United Kingdom) is selected.

In some embodiments, the sustained delivery device comprises a delivery system disclosed in U.S. Pat. No. 5,270,300 ("Hunziker"), which is incorporated by reference in its entirety.

In some embodiments, the sustained delivery device comprises the co-polymer poly-DL-lactide-co-glycolide (PLG). Preferably, the formulation is manufactured by combining the cycline compound, the co-polymer and a solvent to form a droplet, and then evaporating the solvent to form a microsphere. A plurality of microspheres are then combined in a biocompatible diluent. Preferably, the cycline compound is released from the co-polymer by its diffusion therethrough and by the biodegradation of the co-polymer. In some embodiments hereof, the ProLease™ technology of Alkermes (Cambridge, Mass.) is selected.

A sustained release device can comprise a hydrogel. Hydrogels can also be used to deliver the cycline compound in a time-release manner to the disc environment. A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. The hydrogels employed in this invention rapidly solidify to keep the cycline compound at the application site, thereby eliminating undesired migration from the disc. The hydrogels are also biocompatible, e.g., not toxic, to cells suspended in the hydrogel.

A "hydrogel-cycline composition" is a suspension of a hydrogel containing a desired cycline compound. The hydrogel-cycline composition forms a uniform distribution of the cycline compound with a well-defined and precisely controllable density. Moreover, the hydrogel can support very large densities of cycline compounds. In addition, the hydrogel allows diffusion of nutrients to, and waste products away from, the cycline compound, which promotes tissue growth.

Hydrogels suitable for use in the present invention include water-containing gels, i.e., polymers characterized by hydrophilicity and insolubility in water. See, for instance, "Hydrogels" in *Concise Encyclopedia of polymer Science and Engineering*, Mark et al., eds. (Wiley and Sons), pp. 458-459 (1990), the disclosure of which is incorporated herein by reference in its entirety. Although their use is optional in the present invention, the inclusion of hydrogels can be highly advantageous since they tend to contribute a number of desirable qualities. By virtue of their hydrophilic, water-containing nature, hydrogels can:

a) house viable cells, such as mesenchymal stem cells, and
b) redistribute the load bearing and load transmission capabilities of the disc.

In one embodiment, the hydrogel is a fine, powdery, synthetic hydrogel. Suitable hydrogels exhibit an optimal combination of such properties as compatibility with the matrix polymer of choice, and biocompatability. The hydrogel can include any, i.e., one or more, of the following: polysaccharides, proteins, polyphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, poly(vinyl acetate), and sulfonated polymers.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

In some embodiments, the sustained delivery device includes a polymer selected from the group consisting of PLA, PGA, PCL, and mixtures thereof.

If the half-life of the cycline compound within the disc is relatively long, then it may be assumed that a relatively small dose of the cycline compound can be administered into the disc. In this condition, the slow depletion of the cycline compound would not cause the cycline compound to fall below therapeutically effective levels until an extended period of time has elapsed.

In some embodiments in which cycline compounds have long half-lives within the disc space, the dose administered can be very small.

Therefore, in some embodiments, the cycline compound is provided in a dose of less than about 100 mg. If only about 2 mg is needed per day (to provide a transdiscal concentration of at least about 2 mg/disc), then the upper range of this dose should last over one month. In one embodiment, the amount is less than about 50 mg, for example, less than about 20 mg, e.g., less than 10 mg. The smaller amounts available by this route reduce the chances of deleterious side effects of the cycline compound. In one embodiment, the cycline compound provided in these smaller amounts is doxycycline.

In one embodiment, the formulation comprising the cycline compound is administered in an amount of less than 1 cc.

In some embodiments, the formulation of the present invention is administered directly into the disc through the outer wall of the annulus fibrosus. In some embodiments, the direct administration includes depositing the formulation in the nucleus pulposus portion of the disc. In this condition, the fibrous nature of the annulus fibrosus that surrounds the nucleus pulposus will help keep the cycline compound contained within the disc.

In some embodiments, the formulation of the present invention is injected into the disc through a small bore needle. In some embodiments, the needle has a bore of about 22 gauge or less, so that the possibilities of producing a herniation are mitigated. For example, the needle can have a bore of about 24 gauge or less (i.e., a maximum gauge of 24 gauge), so that the possibilities of producing a herniation are even further mitigated.

If the volume of the direct injection of the formulation is sufficiently high so as to cause a concern of overpressurizing the nucleus pulposus, then it is preferred that at least a portion of the nucleus pulposus be removed prior to direct injection. In some embodiments, the volume of removed nucleus pulposus is substantially similar to the volume of the formulation to be injected. For example, the volume of removed nucleus pulposus can be within about 80-120% of the volume of the formulation to be injected. In addition, this procedure has the added benefit of at least partially removing some degenerated disc from the patient.

In other embodiments, the formulation is delivered into the disc space through the endplate of an opposing vertebral body. This avenue eliminates the need to puncture the annulus fibrosus, and so eliminates the possibility of herniation.

Although the cycline compound may therapeutically treat the disc by binding a cytokine, thereby reducing pain and arresting degradation of the ECM, it is believed that at least some of these cycline compounds do not help repair the damage done by the cytokine to the ECM.

Therefore, there may be a need to provide a therapy that also helps repair the ECM.

In accordance with the present invention, there is provided a method of treating degenerative disc disease in an intervertebral disc having a nucleus pulposus, comprising:
  a) transdiscally administering cycline compound into a degenerating disc; and
  b) transdiscally administering at least one additional therapeutic agent in an amount effective to at least partially repair the disc.

In accordance with one aspect of the invention, both the cycline compound and at least one therapeutic agent (i.e., substance) are locally administered into the disc (i.e., the disc tissue). There can be, for example, one additional therapeutic agent, i.e., a second therapeutic agent, or there can be multiple therapeutic agents (e.g., third and fourth additional therapeutic agents).

In some embodiments, the cycline compound and additional therapeutic agent are administered simultaneously. In others, the cycline compound is administered first. In still others, an additional therapeutic agent is administered first.

Other compounds which may be added to the disc include, but are not limited to: vitamins and other nutritional supplements; hormones; glycoproteins; fibronectin; peptides and proteins; carbohydrates (simple and/or complex); proteoglycans; antiangiogenins; oligonucleotides (sense and/or antisense DNA and/or RNA); bone morphogenetic proteins (BMPs); demineralized bone matrix (DBM); antibodies (for example, to infectious agents, tumors, drugs or hormones); gene therapy reagents and anti-cancer agents. Genetically altered cells and/or other cells may also be included in the matrix of this invention. If desired, substances such as pain killers and narcotics may also be admixed with the polymer (or other injectable) for delivery and released to the disc space.

Healthy cells can be introduced into the disc that can at least partially repair any damage done to the disc during the degenerative process. In some embodiments, these cells are introduced into the nucleus pulposus and ultimately produce new extracellular matrix for the nucleus pulposus. In others, these cells are introduced into the annulus fibrosus and produce new extracellular matrix for the annulus fibrosus.

In some embodiments, these cells are obtained from another human individual (allograft), while in other embodiments, the cells are obtained from the same individual (autograft). In some embodiments, the cells are taken from an intervertebral disc (for example, nucleus pulposus cells or annulus fibrosus cells), while in others, the cells are taken from a non-disc tissue (and may be, for example, mesenchymal stem cells or chondrocytes). In other embodiments, autograft chondrocytes (such as from the knee, hip, shoulder, finger or ear) may be used.

In one embodiment, when viable cells are selected as an additional therapeutic substance, the viable cells comprise mesenchymal stem cells (MSCs). MSCs provide a special advantage for administration into a degenerating disc because it is believed that they can more readily survive the relatively harsh environment present in the degenerating disc and that they have a desirable level of plasticity that allows them to proliferate and differentiate into the desired cells.

In some embodiments, the mesenchymal stem cells are obtained from bone marrow, such as autologous bone marrow. In others, the mesenchymal stem cells are obtained from adipose tissue, for example, autologous adipose tissue.

In some embodiments, the mesenchymal stem cells injected into the disc are provided in an unconcentrated form (such as from fresh bone marrow). In others, they are provided in a concentrated form. When provided in concentrated form, they can be uncultured. Uncultured, concentrated MSCs can be readily obtained by centrifugation, filtration, or immunoabsorption. When filtration is selected, the methods disclosed in U.S. Pat. No. 6,049,026 ("Muschler"), which is incorporated by reference in its entirety, can be used. In some embodiments, the matrix used to filter and concentrate the MSCs is also administered into the nucleus pulposus. If this matrix has suitable mechanical properties, it can be used to restore the height of the disc space that was lost during the degradation process.

In some embodiments, growth factors are additional therapeutic agents. As used herein, the term "growth factor" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; members of the insulin-like growth factor (IGF) family, including IGF-I and IGF-II; the TGF-β superfamily, including TGF-β1, 2 and 3 (including MP-52); osteoid-inducing factor (OIF); angiogenin(s); endothelins; hepatocyte growth factor and keratinocyte growth factor; members of the bone morphogenetic proteins (BMPs) BMP-1, BMP-3; BMP-2; OP-1; BMP-2A, BMP-2B, BPM-7 and BPM-14; HBGF-1 and HBGF-2; growth differentiation factors (GDFs); members of the hedgehog family of proteins, including indian, sonic and desert hedgehog; ADMP-1; members of the interleukin (IL) family, including IL-1 thru IL-6; GDF-5, and members of the colony-stimulating factor (CSF) family, including CSF-1, G-CSF, and GM-CSF and isoforms thereof. In one embodiment, the growth factor is administered in an amount effective to repair disc tissue.

In some embodiments, the growth factor is selected from the group consisting of TGF-β, bFGF, and IGF-1. These growth factors are believed to promote regeneration of the nucleus pulposus. In one embodiment, the growth factor is TGF-β. In one embodiment, TGF-β is administered in an amount of between about 10 ng/ml and about 5000 ng/ml, for example, between about 50 ng/ml and about 500 ng/ml, e.g., between 100 ng/ml and about 300 ng/ml.

In some embodiments, platelet concentrate is provided as an additional second therapeutic agent. A growth factor can be provided by platelet concentrate. In one embodiment, the growth factors released by the platelets are present in an amount at least two-fold (e.g., four-fold) greater than the amount found in the blood from which the platelets were taken. In some embodiments, the platelet concentrate is autologous. In some embodiments, the platelet concentrate is platelet rich plasma (PRP). PRP is advantageous because it contains growth factors that can restimulate the growth of the ECM, and because its fibrin matrix provides a suitable scaffold for new tissue growth.

In some embodiments, an additional therapeutic substance is a high specificity cytokine antagonist ("HSCA").

In some embodiments, the HSCA inhibits the cytokine by preventing its production. In some embodiments, the HSCA inhibits the cytokine by binding to a membrane-bound cytokine. In others, the HSCA inhibits the cytokine by binding to a solubilized, e.g., soluble cytokine. In some embodiments, the HSCA inhibitor inhibits the cytokine by both binding to membrane bound cytokine and to solubilized cytokine. In some embodiments, the HSCA is a monoclonal antibody ("mAb"). The use of mAbs is highly desirable since they can bind specifically to a certain target protein and to no other proteins. In some embodiments, the HSCA inhibits the cytokine by binding to a natural receptor of the target cytokine. In some embodiments, the cytokine is a pro-inflammatory cytokine. For example, the high specificity cytokine antagonist is selected from the group consisting of an HSCA of TNF-α, and an HSCA of an interleukin.

In some embodiments, the HSCA is a specific inhibitor (e.g., a high specificity antagonist (HSA)) of TNF-α. Preferred TNF-α antagonists include, but are not limited to, the following: etanercept (ENBREL®-Amgen); infliximab (REMICADE®-Johnson and Johnson); D2E7, a human anti-TNF-α monoclonal antibody (Knoll Pharmaceuticals, Abbott Laboratories); CDP 571 (a humanized anti-TNF-α IgG4 antibody); CDP 870 (an anti-TNF-α humanized monoclonal antibody fragment), both from Celltech; soluble TNF-α: receptor Type I (Amgen); pegylated soluble TNF-α receptor Type I (PEGs TNF-α-R1) (Amgen); and onercept, a recombinant TNF-α binding protein (r-TBP-1) (Serono). In one embodiment, the high specificity antagonist of TNF-α is an inhibitor of soluble TNF-α. In one embodiment, the high specificity antagonist of TNF-α is an inhibitor of TNF-α synthesis. In one embodiment, the high specificity antagonist of TNF-α is an inhibitor of a natural receptor of TNF.

In some embodiments, the HSCA is a specific inhibitor (e.g., a high specificity antagonist) of an interleukin, e.g., a pro-inflammatory interleukin. Preferably, the target interleukin is selected from the group consisting IL-1, IL-1β, IL-2, IL-6, IL-8, IL-12 and IL-19. Preferred antagonists include, but are not limited to, Kineretg (recombinant IL 1-RA, Amgen), IL1-Receptor Type 2 (Amgen) and IL-1 Trap (Regeneron).

Since many pro-inflammatory proteins play a role in disc degeneration, and antagonists thereof are preferably highly specific, it is further believed that injecting at least two of the highly specific antagonists of the present invention directly into the disc would be advantageous.

Therefore, in accordance with the present invention, there is provided a method of treating degenerative disc disease in an intervertebral disc having a nucleus pulposus, comprising administering into an intervertebral disc a formulation comprising:
  i) a cycline compound; and
  ii) at least two highly specific antagonists of pro-inflammatory cytokines selected from the group consisting of TNF-α, an interleukin (e.g., IL-1, Il-6 and IL-8), FAS, an FAS ligand, and IFN-gamma.

In one embodiment, at least one of the substances is an antagonist of TNF-α. In one embodiment, the other substance is an antagonist of an interleukin.

It is further believed that transdiscal administration of an effective amount of other high specificity antagonists of pro-inflammatory processes would also help provide therapy to the patient having DDD. In many embodiments, the transdiscal administration comprises administration of an effective amount of a high specificity antagonist of an enzyme, preferably of a kinase.

In some embodiments, the additional therapeutic substance is a high specificity antagonist (HSA) (i.e., inhibitor) of p38 kinase. It is believed that the p38 kinase site regulates the production of TNF-α, IL-1 and COX-2 enzyme. The inhibition of p38 MAP kinase is believed to block production of both TNF-α and Il-2, both of which are pro-inflammatory cytokines. The small molecule inhibitors of p38 MAP kinase are very specific and potent (~nM). Without wishing to be tied to a theory, it is believed that inhibition of p38 should not block TGF signaling or TGF activity. It is further believed that p38 inhibitors may also block induction of some metalloproteinases, COX-2 and NO synthetase. It is further believed that p38 inhibitors do not inhibit interleukins involved in immune cell proliferation such as IL-2. Preferably, it is provided in a 10 nM to 10 uM dose. Some high specificity antagonists of p38 kinase are disclosed in Zhang, *J. Biol. Chem.*, 272(20): 13397-402 (May 16, 1997); Pargellis, *Nature Structural Biology*, 9(4): 268-272 (April 2002) and Chae, *Bone*, 28(1): 45-53 (January 2001), and in U.S. Pat. Nos. 6,541,477 (Goehring) and 5,965,583 (Beers), which are hereby incorporated by reference in its entirety. Preferably, the HSA of p38 kinase is administered in a dosage to produce a local tissue concentration of between about 5 ug/kg and about 50 ug/kg.

In some embodiments, the p38 kinase inhibitor (i.e., HSA of p38 kinase) is selected from the group consisting of:
  a) diaryl imidizole;
  b) N,N'-diaryl urea (such as those molecules from Bayer, Boehringer Ingelheim and Vertex);
  c) N,N-diaryl urea (such as those molecules from Vertex);
  d) benzophenone (such as those molecules from Leo Pharmaceuticals);
  e) pyrazole ketone (such as those molecules from Hoffman-LaRoche);
  f) indole amide (such as those molecules from GlaxoSmithKline and Scios);
  g) diamides (such as those molecules from AstraZeneca);
  h) quinazoline (such as those molecules from GlaxoSmithKline);

i) pyrimido [4,5-d]pyrimidinone (such as those molecules from GlaxoSmithKline and Hoffman LaRoche); and
j) pyridylamino-quinazolines (such as those molecules from Scios).

In some embodiments, the p38 kinase inhibitor is selected from the group consisting of:
a) SK&F 86002;
b) SB 203580;
c) L-167307;
d) HEP 689;
e) SB220025;
f) VX-745;
g) SU4984;
h) RWJ 68354;
i) ZM336372;
j) PD098059;
k) SB235699; and
l) SB220025.

Members of this group are described, for example, in Zhang et al., supra, Pargellis et al., supra, Chae et al., supra and Cirillo et al., *Current Topics in Medicinal Chemistry*, 2:1021-1035 (2002), Boehm et al., *Exp. Opin. Ther. Patents*, 10(1):25-38 (2000), and Lee et al., *Immunopharmacology*, 47:185-2001 (2000).

In some embodiments, the p38 kinase inhibitor is characterized as a 1-aryl-2-pyridinyl heterocycle. In some embodiments, the 1-aryl-2-pyridinyl heterocycle is selected from the group consisting of:
a) 4,5 substituted imidazole;
b) 1,4,5 substituted imidizole;
c) 2,4,5 substituted imidizole;
d) 1,2,4,5 substituted imidizole; and
e) non-imidizole 5-membered ring heterocycle.

In some embodiments, the p38 kinase inhibitor has at least 3 cyclic groups.

In some embodiments, the p38 kinase inhibitor is selected from the group consisting of a molecule that is readily soluble in water and a substantially water insoluble molecule. In some embodiments, the highly specific antagonist is a p38 kinase inhibitor that is a substantially water insoluble molecule. The substantially water insoluble p38 inhibitor may be advantageous in that, if injected into the nucleus pulposus, it will remain in the nucleus pulposus as a solid and only slightly solubize over time, thereby providing sustained release.

In some embodiments, formulation comprises a cytokine compound and at least one highly specific antagonist (HSA) selected from the group consisting of:
i) an inhibitor of a pro-inflammatory interleukin;
ii) an inhibitor of TNF-α synthesis;
iii) an inhibitor of membrane-bound TNF-α;
iv) an inhibitor of a natural receptor of TNF-α;
v) an inhibitor of NO synthase;
vi) an inhibitor of $PLA_2$ enzyme;
vii) an anti-proliferative agent;
viii) an anti-oxidant;
ix) an apoptosis inhibitor selected from the group consisting of EPO mimetic peptides, EPO mimetibodies, IGF-I, IGF-II, and caspase inhibitors;
x) an inhibitor of MMPs; and
xi) a p38 kinase inhibitor.

In some embodiments, an additional therapeutic substance is an effective amount of a high specificity antagonist of the COX-2 enzyme. It is believed that the COX-2 enzyme is a regulator of the production of prostaglandins, which are involved both in inflammation and the generation of pain.

Typical high specificity antagonists of the COX-2 enzyme include Celecoxib (Searle); Rofecoxib (Merck); Meloxican (Boehringer Manheim); Nimesulide; diclofenac; and Lodine.

In some embodiments, an additional therapeutic substance is an effective amount of a high specificity antagonist of the NO synthase enzyme. It is believed that the NO synthase enzyme regulates the production of NO, which is known to have pro-inflammatory affects. Some high specificity antagonists of NO synthase are N-iminoethyl-L-lysine (L-NIL), and $N^G$-monomethyl-L-arginine. In some embodiments, the high specificity antagonists of NO synthase may be administered systemically.

In some embodiments, an additional therapeutic substance is an effective amount of a high specificity anti-oxidant. It is believed that oxidants degrade the nucleus pulposus extracellular matrix. Typical anti-oxidants include free radical scavengers and superoxide dismutase enzymes.

In some embodiments, the high specificity antioxidants may be administered systemically.

In some embodiments, an additional therapeutic agent is an effective amount of a high specificity anti-proliferative agent that would also help provide therapy to the patient having DDD. It is believed that antiproliferative agents may have an effect on inflammation by affecting inflamed tissues that would limit the production of inflammatory cytokines. In some embodiments, the high specificity anti-proliferative is selected from the group consisting of a) rapamycin; b) an inhibitor of cyclin dependent kinase 9 (cdk); and c) statins (such as MEVASTATIN™ and LOVASTATIN™). When rapamycin is selected, in some embodiments, a dosage produces a local tissue concentration of between about 0.5 ug/kg and about 50 ug/kg.

Rapamycin is a potent inhibitor of downstream signaling of TOR (target of Rapamycin) proteins. As such, it is responsible for coordinating the balance between protein synthesis and protein degradation. It is believed that DDD is propagated by a loss of balance between extracellular matrix synthesis and degradation. Since TOR proteins regulate multiple metabolic pathways, rapamycin may stabilize the balance of the cycle. Rapamycin may also directly effect the proliferation and subsequent immune reaction of chondrocytes. In addition, degenerative chondrocytes demonstrate a low level of proliferative activity by contrast to normal chondrocytes that show no activity. This is thought to lead to chondrocyte clustering within the cartilage. Rapamycin could function to eliminate the atypical chondrocyte proliferation. In one embodiment, it is provided in about a 0.1 to 10 μM dose.

A cdk inhibitor may directly effect the proliferation and subsequent immune reaction of chondrocytes. A cdk inhibitor may also have a direct effect on chondrocyte clustering which is known to be a characteristic degenerative event. Exemplary cdk inhibitors include flavopiridol, roscovitine, and compounds disclosed in PCT Patent Publication No. WO 02/057240 (Lin) and U.S. provisional patent application 60/257,703, which are incorporated by reference herein in their entirety. In one embodiment, it is provided in about a 1 to 10 μM dose.

In some embodiments, an additional therapeutic substance is a highly specific anti-apoptosis molecule (i.e., an apoptosis inhibitor). It is believed these molecules will serve to protect against chondrocyte apoptosis. In some embodiments, compounds include EPO, erythropoetin mimetic peptides, EPO mimetibodies, IGF-I, IGF-II, and caspase inhibitors (e.g., a highly specific caspase inhibitor).

Non-steroidal anti-inflammatory drugs (NSAIDs) may also be selected as an additional therapeutic agent. In some embodiments, the NSAID is anabolic, and is, for example, selected from the group consisting of TOLMETIN™ (Ortho-MacNeil), SUPROL™ (Johnson & Johnson), and Tiaprofenic acid (available from Roussel Labs). Preferably, the anabolic NSAID is administered in a dosage sufficient to produce an initial local tissue concentration of between about 5 ug/kg and about 500 ug/kg. In some embodiments, the NSAID is a dual inhibitor of both the COX and LOX pathways, and is preferably TEPOXALIN™ (Johnson & Johnson).

In addition, anti-cathepsins may also be used in accordance with the present invention. It is believed that inhibition of these enzymes inhibits the breakdown of the extracellular matrix. In one embodiment, the antagonists inhibit a cathepsin selected from the group consisting of cathepsin B, cathepsin L and cathepsin K.

In some embodiments, the cycline compound is combined in the formulation with a viscosupplement. The viscosupplement has characteristics substantially similar to that of natural healthy nucleus pulposus ECM.

Preferably, the viscosupplement is selected from the group consisting of hyaluronic acid and hyaluronate (either cross-linked or uncross-linked). In some embodiments, the viscosupplement is ARTHREASE™ (DePuy Ltd., Leeds, U.K.). In some embodiments, the viscosupplement is a hyaluronic acid selected from the hyaluronic acids disclosed in U.S. Ser. No. 09/298,539, entitled "Method of Treating Diseased, Injured or Abnormal Cartilage with Hyaluronic Acid and Growth Factors" (Radomsky et al.), which is incorporated by reference in its entirety.

Preferably, the viscosupplement comprises a glycosaminoglycans (GAGS). GAGS are biopolymers consisting of repeating polysaccharide units, and are present in nature on the cell surface as well as in the extracellular matrix of animals. GAGS are long unbranched polysaccharides containing a repeating disaccharide unit. The disaccharide unit contains either of two modified sugars, N-acetylgalactosamine or N-acetylglucosamine and a uronic acid such as glucuronate or iduronate. GAGS are highly negatively charged molecules, with extended conformation that imparts high viscosity to the solution. In addition, to high viscosity, GAGS routinely possess low compressibility, which makes these molecules ideal for a lubricating fluid in the joints. At the same time, their rigidity provides structural integrity to cells and provides passageways between cells allowing for cell migration.

Hyaluronic acid (HA) is a high molecular weight polysaccharide of N-acetyl glucosaime and glucuronic acid molecules that is naturally occurring in all mammals in a variety of tissue and some bacterial species. For the purposes of this invention, HA includes any derivatives such as hyaluronan and hyaluronic acid itself with $H^+$ ion attached to the $COO^-$ group, and salts of hyaluronic acid whereby another positive ion replaces the H+ ion, for example, as with $Na^+$ which forms sodium hyaluronate. Also included in the definition of HA is any physically or chemically cross-linked hyaluronic acid or derivative. HA is unique among the GAGS in that it does not contain any sulphate and is not found covalently attached to proteins as a proteoglycan. HA polymers are very large with molecular weights of between about 100,000 and 10,000,000 and can displace a large volume of water. For the purposes of the present invention, one embodiment includes a non-cross linked HA with a molecular weight of 0.5-10 M Dalton.

In some embodiments, the viscosupplement is selected from the group consisting of hyaluronic acid and hyaluronate (either cross-linked or uncross-linked).

In some embodiments, cartilage cells (which may be, for example, from either an allogeneic or autologous source) or mesenchymal stem cells, may be genetically modified to produce a cartilage anabolic agent which can be chosen from the list of growth factors named herein.

Recent work has shown that plasmid DNA will not elicit an inflammatory response as does the use of viral vectors. Genes encoding cartilage (anabolic) agents such as BMP may be efficacious if injected into the joint. In addition, overexpression of any of the growth factors provided herein or other agents such as a tissue inhibitor of MMPs (TIMP) that would limit local MMP activity would have positive effects on chondrocyte and ECM protection. In some embodiments, the TIMP is selected from the group consisting of TIMP-1 and TIMP-2. In some embodiments, the TIMP is autologous and is concentrated by filtration, centrifugation or by immuno-attachment processes. In other embodiments, the TIMP is manufactured recombinantly, and is preferably present in a concentration of at least 1000 times that found in the patient. In one embodiment, the plasmid contains the genetic code for human TGF-β or EPO.

Accordingly, in some embodiments, the additional therapeutic agent is selected from the group consisting of:
  i) a growth factor,
  ii) viable cells, and
  iii) plasmid DNA.

In some embodiments, the formulation comprises a suitable biocompatible carrier such as saline. In some embodiments, the carrier is selected from the carriers disclosed in U.S. Pat. No. 6,277,969 ("Le"), which is incorporated by reference in its entirety. In some embodiments, the formulation includes a solvent, for example, a solvent selected from the group consisting of DMSO and ethanol.

In some embodiments, the formulation is administered through a drug pump.

In some embodiments, the formulation further comprises a buffer. This buffer is preferably provided in an amount effective to substantially maintain the pH balance of the nucleus pulposus.

Also in accordance with the present invention, there is provided a formulation for treating degenerative disc disease, comprising:
  a) a cycline compound, and
  b) an additional therapeutic agent selected from the group consisting of:
    i) a growth factor, and
    ii) viable cells.

Because the causes of back pain (e.g., low back pain) may be myriad, it would be useful for the clinician to first perform a diagnostic test in order to confirm that the targeted disc in fact possesses high levels of the targeted pro-inflammatory cytokine and/or MMPs prior to providing the injection of the cycline compound.

In one embodiment, the diagnostic test comprises a non-invasive diagnostic test comprising using an MRI (magnetic resonance imaging).

Preferably, the clinician would first perform a discogram in order to identify which disc or discs are responsible for the patient's low back pain. Next, the clinician would perform an invasive or non-invasive test upon the targeted disc in order to confirm the presence of or quantify the level of the pro-inflammatory cytokine and MMPs.

In one embodiment, the diagnostic test comprises an invasive test in which a portion of the disc is removed and analyzed. In some embodiments, the clinician removes a portion of the nucleus pulposus. In some embodiments, the clinician removes a portion of the annulus fibrosus. In one embodiment, the removed material is a portion of the nucleus pulposus. The presence of the pro-inflammatory cytokine and/or MMPs in the removed material may be detected by procedures including, but not limited to, electrophoresis or an enzyme-linked immunoabsorbent assay (ELISA) (as per Burke, Br. JBJS, 84-B(2): 196 (2002).

In one embodiment, after determining the levels of the pro-inflammatory cytokine and MMPs in the degenerating disc, the clinician will preferably proceed to compare these diagnosed levels against pre-determined levels of the pro-inflammatory cytokine and MMPs. If the diagnosed level of the pro-inflammatory cytokine and MMPs exceeds their pre-determined levels, then the clinician may conclude that these higher levels are causing unwanted inflammatory and degradatory action and proceed to inject directly a cycline compound into the disc.

In some embodiments, a bioMEMS device containing a "lab on a chip" used in the diagnostic test.

In some embodiments, the predetermined level for an interleukin is at least 100 pg/ml. In some embodiments, the predetermined level for IL-6 is at least 250 pg/ml. In some embodiments, the predetermined level for IL-8 is at least 500 pg/ml. In some embodiments, the predetermined level for PGE2 is at least 1000 pg/ml. In some embodiments, the predetermined level for TNF-α is at least 500 pg/ml.

It would also be useful to be able to determine whether directly administering the cycline compounds of the present invention was, in fact, efficacious. Accordingly, one can, for example, measure the level of cytokine and/or MMP remaining in the disc after administration.

In accordance with the present invention, there is also provided a method of therapeutically treating a degenerating intervertebral disc of a patient, comprising:
a) determining a level of a pro-inflammatory protein within the disc;
b) comparing the level against a pre-determined level of the pro-inflammatory protein; and
c) injecting a cycline compound into the disc.

The present invention can also be used to prevent degeneration of an intervertebral disc in a human individual, namely, by following a procedure comprising:
a) determining a genetic profile of the individual;
b) comparing the genetic profile of the individual against a pre-determined genetic profile level of at-risk humans;
c) determining that the individual is an at-risk patient; and
d) injecting a cycline compound into a disc of the individual.

EXAMPLE I

This non-limiting prophetic example describes how to administer transdiscally a formulation comprising a cycline compound into a nucleus pulposus of a degenerating disc.

First, a clinician uses a diagnostic test to verify that a particular disc within a patient has high levels of a particular pro-inflammatory cytokine and/or MMPs.

Next, the clinician provides a local anesthetic (such as 5 ml lidocaine) to the region dorsal of the disc of concern to reduce subcutaneous pain.

Next, the clinician punctures the skin of the patient dorsal to the disc of concern with a relatively large (e.g., 18-19 gauge) needle having a stylet therein, and advances the needle through subcutaneous fat and dorsal sacrolumbar ligament and muscles to the outer edge of the intervertebral disc.

Next, the stylet is removed from the needle.

In one embodiment, the portion of the nucleus pulposus is removed prior to administering the cycline compound.

Next, the clinician receives a syringe having a smaller gauge needle adapted to fit within the larger gauge needle. This needle is typically a 22 or 24 gauge needle. The barrel of the syringe contains the formulation of the present invention. The formulation contains about 50 mg/ml of doxycycline.

Next, the physician advances the smaller needle co-axially through the larger needle and past the distal end of the larger needle, thereby puncturing the annulus fibrosus. The smaller needle is then further advanced into the center of the nucleus pulposus. Finally, the clinician depresses the plunger of the syringe, thereby injecting between about 0.1 and about 1 ml of the formulation into the nucleus pulposus.

EXAMPLE II

This non-limiting prophetic example is substantially similar to that of Example I, except that the formulation comprises a sustained release device comprising the co-polymer poly-DL-lactide-co-glycolide (PLG). The formulation contains doxycycline.

While this invention has been particularly shown and described with references to preferred embodiments thereof, it will be understood by those skilled in the art that various changes in form and details may be made therein without departing from the scope of the invention encompassed by the appended claims.

What is claimed is:

1. A formulation for treating degenerative disc disease, comprising:
a) a cycline compound selected from the group consisting of doxycycline, lymecycline and minocycline; and
b) an additional therapeutic agent selected from the group consisting of a growth factor and viable mesenchymal stem cells.

2. The formulation of claim 1, wherein the additional therapeutic agent is said viable mesenchymal stem cells.

3. The formulation of claim 2, wherein the mesenchymal stem cells are autologous.

4. The formulation of claim 3, wherein the mesenchymal stem cells are provided in a concentrated form.

5. The formulation of claim 1, wherein the additional therapeutic agent is a growth factor.

6. The formulation of claim 1, wherein the cycline compound is doxycycline.

7. The formulation of claim 1, wherein the cycline compound is minocyline.

8. The formulation of claim 1, wherein said cycline compound is released from a sustained delivery device.

9. The formulation of claim 8, wherein said sustained release device is adapted to remain within the intervertebral disc for at least 1 month.

10. The formulation of claim 8, wherein said sustained release device is adapted to remain within the intervertebral disc for at least 2 months.

11. The formulation of claim 8, wherein said sustained release device is adapted to remain within the intervertebral disc for at least 6 months.

12. A method of therapeutically treating a degenerating intervertebral disc of a patient, comprising:
a) determining a level of a pro-inflammatory protein within the disc,
b) comparing the level against a pre-determined level of the pro-inflammatory protein, and
c) injecting a cycline compound into the disc.

13. The method of claim 12, wherein the proinflammatory protein is an interleukin.

14. The method of claim 12, wherein the predetermined level for the interleukin is at least 100 pg/ml.

15. The method of claim 12, wherein the proinflammatory protein is interleukin-6 or interleukin-8.

16. The method of claim 15, wherein the proinflammatory protein is interleukin-6 and the predetermined level for the interleukin-6 is at least 100 pg/ml.

17. The method of claim 15, wherein the proinflammatory protein is interleukin-6 and the predetermined level for the interleukin-6 is at least 250 pg/ml.

18. The formulation of claim 5, wherein the growth factor is a transforming growth factor-β (TGF-β) or a bone morphogenetic protein (BMP).

19. The formulation of claim 3, wherein the mesenchymal stem cells are uncultured.

20. A method of preventing degeneration of an intervertebral disc in a human individual, comprising:
    a) determining a genetic profile of the individual,
    b) comparing the genetic profile of the individual against a pre-determined genetic profile level of at-risk humans,
    c) determining that the individual is an at-risk patient, and
    d) injecting a cycline compound into a disc of the individual.

* * * * *